United States Patent [19]

Swift

[11] 4,353,835

[45] Oct. 12, 1982

[54] PROCESS FOR HYDROGENATING UNSATURATED CARBOXYLIC ACIDS AND CARBOXYLIC ACID ESTERS

[75] Inventor: Harold E. Swift, Gibsonia, Pa.

[73] Assignee: Gulf Research & Development Company, Pittsburgh, Pa.

[21] Appl. No.: 250,236

[22] Filed: Apr. 2, 1981

[51] Int. Cl.$^3$ ............................................. C11C 3/12
[52] U.S. Cl. ................................... 260/409; 562/606; 560/265
[58] Field of Search ....................... 260/409; 562/606; 560/265

[56] References Cited

U.S. PATENT DOCUMENTS 3,729,429 4/1973 Robson ................................ 252/454
4,210,768 7/1980 Swift .................................... 585/259

Primary Examiner—John F. Niebling
Attorney, Agent, or Firm—Deane E. Keith; Forrest D. Stine; Donald L. Rose

[57] ABSTRACT

A process for hydrogenating unsaturated carboxylic acids and esters of unsaturated carboxylic acids such as fatty acids which comprises reacting the unsaturated composition with hydrogen in contact with a catalyst prepared from a layered complex nickel silicate which has been prepared in a multi-stage procedure comprising reduction in a hydrogen atmosphere, oxidation in an atmosphere containing molecular oxygen and then again reduction in a hydrogen atmosphere.

13 Claims, No Drawings

PROCESS FOR HYDROGENATING UNSATURATED CARBOXYLIC ACIDS AND CARBOXYLIC ACID ESTERS

SUMMARY OF THE INVENTION

This invention relates to a process for hydrogenating unsaturated carboxylic acids and unsaturated carboxylic acid esters which comprises reacting one or a mixture of unsaturated carboxylic acids or unsaturated carboxylic acid esters with hydrogen in contact with a nickel silica catalyst which has been prepared by the treatment of a layered complex metal silicate containing nickel in a three-stage cycle of reduction, oxidation and reduction.

DETAILED DESCRIPTION OF THE INVENTION

The fatty acids are generally obtained by splitting them out of naturally occurring glyceryl esters such as found in fats and oils, or from esters of fatty acids with higher monohydric alcohols such as waxes, or by separating the fatty acids from industrial by-product materials such as tall oil. The resulting fatty acid product after purification, often by distillation at reduced pressure, is generally a mixture of saturated and unsaturated monocarboxylic acids. However, individual fatty acids can also be obtained in a relatively pure state. Many uses require that the fatty acids be saturated. Particular uses may also require that a fat or an oil or even a wax be saturated.

The most successful procedures for the hydrogenation of fatty acids that are in commercial use are batch processes. Such batch processes utilize a finely divided nickel catalyst dispersed throughout the liquid mixture. If a suitable continuous process could be used for this fatty acid hydrogenation in place of a batch procedure, there could be significant savings in material and handling costs. Another significant advantage in a continuous process would result from the elimination of the catalyst separation problems inherent in the batch process. However, to date there does not appear to be a suitable continuous fatty acid hydrogenation process in substantial commercial use.

I have discovered that unsaturated carboxylic acids and unsaturated carboxylic acid esters can be hydrogenated using a catalyst which is prepared by treating a layered complex metal silicate containing nickel in a multi-stage cycle of reduction, oxidation and reduction. More particularly, I have discovered that unsaturated fatty acids and unsaturated fatty acid esters can be hydrogenated in a continuous process with this catalyst, and I have further discovered that the catalyst exhibits high activity and can hydrogenate a significantly greater amount of the unsaturated carboxylic acid in the continuous process than conventional nickel hydrogenation catalysts in batch fatty acid hydrogenation. And a special advantage of this continuous hydrogenation process is the high conversion possible to a hydrogenated product with an iodine value (I.V.) as low as about 1.0 and lower.

The unsaturated carboxylic acids which are suitably hydrogenated by the process described herein can contain from three to about 30 carbon atoms and include the monoethenoid and polyethenoid acids (viz. diethenoid, triethenoid, etc.). But the preferred unsaturated carboxylic acids are the fatty acids containing from about 12 to 22 carbon atoms, particularly those fatty acids which are obtainable from natural sources and are therefore relatively abundant and inexpensive. These carboxylic acids as used in the process can be in a relatively pure state, or they can be in admixture with closely related saturated fatty acids, such as oleic acid admixed with palmitic acid and stearic acid as derived from beef tallow. Other unsaturated fatty acids include lauroleic acid, myristoleic acid, palmitoleic acid, elaidic acid, erucic acid, brassidic acid, linoleic acid, linolelaidic acid, eleostearic acid, linolenic acid, arachidonic acid, ricinoleic acid, licanic acid, and the like. Carboxylic acids other than fatty acids which can be hydrogenated by this process include acrylic acid, crotonic acid, angelic acid, tiglic acid, sorbic acid, and the like.

The unsaturated carboxylic acid esters which can be suitably hydrogenated by this process include, in particular, the glyceryl fatty acid esters containing from one to three unsaturated fatty acid acyl groups such as set out above. These useful glyceryl esters include the monoglycerides, the diglycerides, the triglycerides, and mixtures of these. The carboxylic acid ester can also be the ester of an acid and a monoalcohol in which the unsaturation is in the acid moiety, or in the alcohol moiety, or in both groups.

The hydrogenation catalyst used herein is prepared by subjecting a layered complex metal silicate to a three-step reduction, oxidation and reduction sequence of treatments. This layered complex metal silicate composition is characterized as having repeating units of the structural formula:

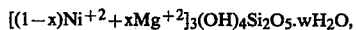

$$[(1-x)Ni^{+2} + xMg^{+2}]_3(OH)_4Si_2O_5 \cdot wH_2O,$$

wherein x is a number from 0 to 0.6, preferably from 0 to 0.4, most preferably 0, this number expressing the atomic fraction of the metals nickel and magnesium, and w is a number from 0 to 4. When x is 0, the composition is known as nickel chrysotile. The chrysotile structure can occur in the shape of tubes (and rods) or as flakes (and curls) or as a mixture of tubes and flakes. For the purpose of preparing a catalyst of high activity for use in the instant hydrogenation process, the tube form or mixtures predominating in the tube form are greatly preferred.

Layered complex metal silicate catalysts are known and have been used, for example, to hydrogenate benzene as in U.S. Pat. No. 3,865,895 and to convert carbon monoxide and hydrogen to methane, as in U.S. Pat. No. 4,022,810. Surface properties of hydrogen reduced metal silicates have been described by Kibby et al in the *Journal of Catalysis* 42, (1976) pages 350 to 359. The preparation of these layered complex metal silicates is described by Noll et al, Kolloid Zeitschrift 157, 1 (1958), and in U.S. Pat. Nos. 3,729,429 and 4,210,768.

In order to prepare the catalyst for use in hydrogenating unsaturated carboxylic acids and unsaturated carboxylic acid esters, it is essential that the layered complex metal silicate catalyst precursor first be reduced in a hydrogen atmosphere, then oxidized in an atmosphere containing oxygen and then finally reduced again in a hydrogen atmosphere. The first and final hydrogenations can be effected by heating the catalyst at a temperature in the range of about 200° to about 600° C., preferably about 300° to about 550° C., for about one to about 24 hours or more, preferably about four to about 12 hours, while maintaining a hydrogen pressure thereon of about 15 to about 1000 pounds per square inch gauge (one psig equals 0.0704 kg per cm$^2$), preferably about 50 to about 500 ponds per square inch gauge. The intermediate oxidation stage is conducted at a temperature of about 100° to about 600° C., preferably about 200° to about 550° C., for about two to about 24 hours or more, preferably about four to about 12 hours, with a gas containing from about two to about 90 volume percent molecular oxygen, preferably from about five to about 20 volume percent molecular oxygen. The active species in the catalyst following this treating sequence is believed to be minute particles of nickel metal dispersed throughout a silica substrate.

Although this catalyst can be used in the hydrogenation of unsaturated carboxylic acids or unsaturated carboxylic acid esters in a batch reaction, it is particularly useful in a continuous hydrogenation operation. The continuous hydrogenation reaction can be carried out in a flow-through reactor in which the catalyst is positioned in the reactor in the form of a bed of discrete particles or granules. In this procedure the liquid feed can be flowed through the catalyst bed or it can be caused to trickle over the catalyst in order to obtain more intimate contact with the catalyst. Or the continuous procedure can be carried out as a slurry in an autoclave provided with a porous filter plate positioned at the reaction outlet. In this latter embodiment a continuous feed stream containing the unsaturated carboxylic acid is fed to the reactor and a continuous stream of the reaction liquid is withdrawn from the reactor. The catalyst in a finely divided or powdered form is dispersed throughout the reaction liquid by suitable agitation. The particle size of the catalyst, the size of the openings in the filter plate and the vigor of the agitation are appropriately intercorrelated to ensure that catalyst particles do not block or cake up on the filter plate.

If desired, the unsaturated carboxylic acid, unsaturated carboxylic acid ester or mixture containing one or more of these compounds can be dissolved in a suitable inert diluent to decrease the fluid viscosity. The diluent should be sufficiently lower boiling in order to ensure easy separation after the hydrogenation. Hydrocarbons such as cyclohexane, n-hexane, n-heptane, and the like are particularly useful. The diluent can comprise up to 90 weight percent of the feed mixture, but it is preferred that the diluent, if present, be no higher than about 50 percent of the mixture in order to maintain a suitable concentration and hydrogenation rate. The lower boiling diluent may at times be useful but it is not generally a necessity. The saturated carboxylic acids (or saturated carboxylic acid esters) having a boiling point similar to the unsaturated acids, which are generally intermixed in the glyceryl esters of the natural oils, do not function herein as lower boiling diluents.

The hydrogenation of the unsaturated acid or the unsaturated ester can be carried out within a temperature range of between about 5° and about 500° C., but preferably the hydrogenation is carried out within a temperature range of between about 50 and about 400° C. The hydrogen pressure in the reactor will be between about 50 and about 5,000 psig, preferably between about 100 and about 1,000 psig. The continuous hydrogenation reaction can suitably be carried out at a liquid weight hourly space velocity (weight of total charge per weight of catalyst) of between about 0.25 and about 20, preferably between about 0.5 and about 5.

DESCRIPTION OF A PREFERRED EMBODIMENT

Example

A commercial sample of distilled tallow acid, which was predominantly a mixture of oleic acid, palmitic acid and stearic acid, having an iodine value (expressed as the number of centigrams of iodine absorbed per gram of sample) of 23.5 was hydrogenated using a catalyst prepared from nickel chrysotile $Ni_3(OH)_4Si_2O_5$ of a minute tubular structure having an average pore radius of 48.9 Angstroms and a surface area by the B.E.T. method of 124.2 square meters per gram. The nickel chrysotile was extruded and sized to 20-30 mesh granules.

The solid granular particles (36.26 g) were placed in a one-half inch I.D. quartz reactor to a depth of about 12 inches. Heating of the reactor was accomplished with a concentric electric furnace. A stream containing 150 cc per minute of hydrogen and 50 cc per minute of nitrogen was flowed through the bed as the reactor was heated. The solid particles reached a temperature of about 500° C. in three hours. The reduction was continued for 20 more hours at 500° C. The reactor was then switched to nitrogen flow at about 100 cc per minute to flush out the hydrogen and then air at about 20 cc per minute was introduced into the nitrogen stream. The oxidation was continued at 500° C. for 40 hours. The oxidized product weighed 30.77 g and by analysis showed a nickel content of 47.5 percent.

The fatty acid hydrogenation was conducted in a 0.515 inch I.D. stainless steel reactor which was provided with an 0.25 O.D. thermowell. Thirty cc of a mixture comprising 20 cc of the oxidized nickel granules (7.77 g of nickel) and 10 cc of 20-30 mesh quartz was positioned about a 50 cc bed of the 20-30 mesh quartz and below a 40 cc bed of the 20-30 mesh quartz. The oxidized nickel granules were then reduced by passing a stream of hydrogen downwardly through the bed at 500° C. for 16 hours. The bed was cooled and the tallow acid hydrogenation reaction was initiated.

The tallow acid feed was introduced into the top of the reactor at an inlet temperature of 125° C. and at a liquid feed rate of 100 cc per hour (LHSV=5/hr) to provide a downflow trickle bed reactor configuration. Hydrogen was flowed downwardly at a pressure of 500 psig. The molar ratio of the liquid feed and the hydrogen was about 1:1. The initial product had an I.V. of about 0.2 but slowly elevated with time. After about 160 hours the I.V. of the product had increased to about 1.0. At this time, the inlet temperature was increased to 150° C. and the product I.V. lowered to about 0.3. When the product I.V. had increased to about 1.1 in about 160 hours, the temperature was increased to 175° C. resulting in a drop in the product I.V. to about 0.4. After 400 hours of this hydrogenation procedure, a total quantity of about 40,000 cc of the tallow acid had been hydrogenated at a maximum inlet temperature of 175° C. During the hydrogenation, the maximum bed temperature, i.e. hot spot temperature, was about 5° to 10° C. higher than the inlet temperature. The operating temperature was kept below 200° C. to ensure that no product decomposition occurred. However, it is believed that additional satisfactory hydrogenated product could have been produced without product decomposition.

The resulting 40 liters of hydrogenated tallow acid had an overall iodine value of about 0.62. This continuous hydrogenation procedure resulted in the production of hydrogenated product at a ratio of about 5,150 cc of hydrogenated fatty acid per gram of nickel. In contrast typical batch hydrogenation utilizing a conventional nickel hydrogenation catalyst results in about 1,500 cc of hydrogenated fatty acid of suitable iodine value per gram of nickel.

It is to be understood that the above disclosure is by way of specific example and that numerous modifications and variations are available to those of ordinary skill in the art without departing from the true spirit and scope of the invention.

I claim:

1. A process for hydrogenating unsaturated carboxylic acids and esters of unsaturated carboxylic acids which comprises reacting an unsaturated carboxylic acid, an ester of a carboxylic acid or a mixture thereof with hydrogen in contact with a nickel silica catalyst obtainable from a layered complex nickel silicate characterized as having repeating units of the structural formula:

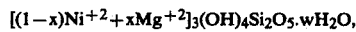

wherein x is a number from 0 to 0.6 and w is a number ranging from 0 to 4, by a multi-stage procedure comprising a first reduction in a hydrogen atmosphere at a temperature of about 200° C. to about 600° C. and a pressure of about 15 to about 1,000 pounds per square inch gauge for a period of at least about one hour, an oxidation in an atmosphere containing molecular oxygen at a temperature of about 100° C. to about 600° C. for a period of at least about two hours using a gas containing from about two to about 90 volume percent molecular oxygen, and then again a reduction in a hydrogen atmosphere at a temperature of about 200° C. to about 600° C. and a pressure of about 15 to about 1,000 pounds per square inch gauge for a period of at least about one hour.

2. The process of claim 1 wherein said process is continuous.

3. The process of claim 2 wherein x is a number from 0 to 0.4 and w is a number from 0 to 4.

4. The process of claim 2 wherein x is 0 and w is a number from 0 to 4.

5. The process of claim 2 wherein said reductions of said layered complex nickel silicate are carried out at a temperature of about 300° C. to about 550° C. and a pressure of about 50 to about 500 pounds per square inch gauge for a period of about four to about 24 hours.

6. The process of claim 2 wherein said oxidation of said layered complex nickel silicate is carried out at a temperature of about 200° C. to about 550° C. for a period of about four to about 24 hours using a gas containing from about five to about 20 volume percent molecular oxygen.

7. The process of claim 2 wherein the unsaturated material is reacted with hydrogen at a temperature of about 5° C. to about 500° C. and a pressure of about 50 to about 5000 pounds per square inch gauge.

8. The process of claim 2 wherein the unsaturated material is reacted with hydrogen at a temperature of about 50° C. to about 400° C. and a pressure of about 100 to about 1,000 pounds per square inch gauge.

9. The process of claims 2 or 4 wherein the unsaturated material comprises one or more unsaturated fatty acids having from about 12 to about 22 carbon atoms.

10. The process of claim 9 wherein the unsaturated fatty acids are selected from monoethenoid acids, polyethenoid acids, and mixtures thereof.

11. The process of claim 9 wherein the unsaturated fatty acid or acids are mixed with one or more saturated fatty acids.

12. The process of claim 9 wherein the unsaturated material comprises oleic acid.

13. The process of claims 2 or 4 wherein the unsaturated material comprises one or more glyceryl esters of one or more unsaturated fatty acids having from about 12 to about 22 carbon atoms.

* * * * *